Figure 1:
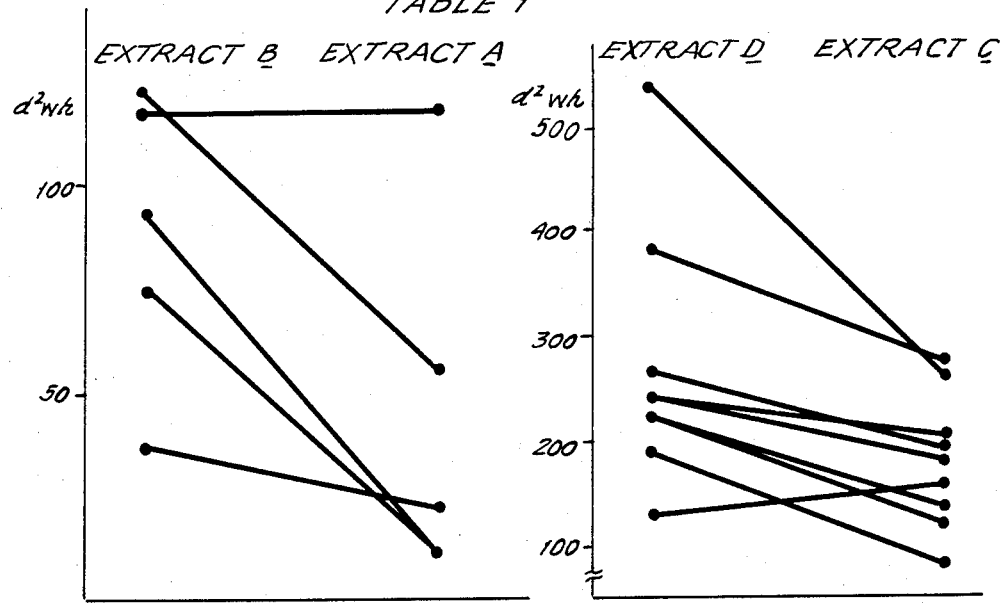

United States Patent [19]

Stevens et al.

[11] Patent Number: 4,600,582
[45] Date of Patent: Jul. 15, 1986

[54] THERAPEUTIC TREATMENT

[75] Inventors: Erik Stevens, Linden-Lubbeek; Ernestina M. Van Hoeyveld, Lubbeek, both of Belgium

[73] Assignee: Tetra Consultants, Inc., New Rochelle, N.Y.

[21] Appl. No.: 415,568

[22] Filed: Sep. 7, 1982

[51] Int. Cl.$^4$ .................. A61K 39/36; A61K 39/00
[52] U.S. Cl. .................. 424/91; 424/88; 514/2; 514/561; 514/169; 514/226; 514/368; 514/615
[58] Field of Search .................. 424/85, 88, 89, 91, 424/92, 181, 246, 305, 311, 319, 320, 86, 87, 101, 177; 252/403; 514/2, 561, 169, 226, 368, 615

[56] References Cited

U.S. PATENT DOCUMENTS

| 4,226,853 | 10/1980 | Marsh | 424/88 |
| 4,258,029 | 3/1981 | Moloney | 424/88 |
| 4,363,818 | 12/1982 | Gottlieb | 424/319 |

FOREIGN PATENT DOCUMENTS

| 1808948 | 7/1969 | Fed. Rep. of Germany | 514/564 |
| 47-1479 | 1/1972 | Japan | 514/561 |

*Primary Examiner*—David M. Naff
*Assistant Examiner*—Shawn P. Foley

[57] ABSTRACT

A method of reducing local adverse reactions which occur at the site of administration of parenterally administrable physiologically active compositions, to patients which comprises, prior to administration thereof, incorporating in said physiologically active compositions, a small but effective amount of a compound of the formulae,

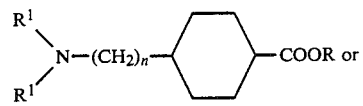

or

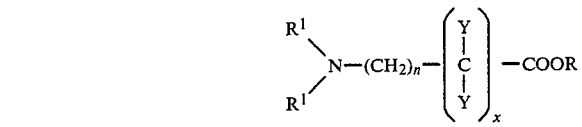

wherein n is an integer of from 1 to 6; $R^1$ is H or lower alkyl; x is 0 or 1; each Y is H; and R is H, lower alkyl or acyl; and the non-toxic pharmaceutically acceptable salts thereof.

5 Claims, 2 Drawing Figures

TABLE 1

TABLE 2

THERAPEUTIC TREATMENT

This invention relates to methods of parenterally administering physiologically active compositions to patients and improved compositions useful for such purposes. More particularly, this invention has as its objective improved and novel methods for parenterally administering liquid, physiologically active compositions to patients and to new compositions useful therefor.

It is well recognized that there are numerous instances in which physiologically active compositions are required to be parenterally administered to patients. Physiologically active compositions may have to be parenterally administered to patients for either therapeutic or diagnostic purposes and physiologically active components of the compositions can encompass a broad spectrum of active materials including such well known materials as biological derivatives, for example, sera, vaccines, toxoids and anti-toxins, allergens, and allergenic extracts; or chemically derived substances, for example, antibiotics, steroids, central nervous system agents, and other like pharmacologically active chemical substances.

When it is determined by the skilled worker that the physiologically active material to be administered is best introduced to the patient being treated by a parenteral route, the physiologically active material is first incorporated into a suitable parenterally administerable composition for this purpose. This parenterally administerable composition is usually in a liquid form and is usually comprised of a suitable, parenterally administerable non-toxic vehicle, for example, water or a combination of water and alcohol, into which has been incorporated the required amount of the desired physiologically active material. The resultant liquid parenterally administerable physiologically active composition is then administered to the patient by the parenteral route selected by the skilled worker, for example, by intramuscular, subcutaneous, intradermal or intravenous route, employing the usual acceptable means for accomplishing this administration, such as a hypodermic needle and syringe. The methods and means of parenterally administering such parenterally administerable compositions to patients are well known to and understood by the worker skilled in the art.

On occasion, as a result of the parenteral administration of these physiologically active compositions, the patient suffers various adverse systemic side effects, for example, swelling and inflammation of the skin and subdermal area surrounding the site of parenteral administration. While these localized systemic adverse reactions are usually not severe or frequent, they do occur with sufficient frequency and intensity in the parenteral administration of certain physiologically active materials, for example, allergenic extracts, insect or snake venoms, certain insoluble antibiotics, and other like materials, to pose a serious problem to the patient being treated. Likewise, the incidence and severity of these adverse reactions may also increase in response to the character of the parenterally administerable vehicle being employed in the final compositions being administered to the patient, for example, vegetable oil vehicles frequently cause such adverse reactions. To date, though many various attempts have been made to reduce or eliminate the occurrence of these adverse reactions, none has been completely satisfactory.

We have discovered a method of substantially reducing or eliminating local adverse reactions occurring at or near the site of administration, as a result of the parenteral administration to patients of liquid physiologically active compositions which comprises, incorporating in said parenterally administerable, liquid, physiologically active compositions, prior to the administration thereof to the patient, a small but effective amount of a compound of the formulae,

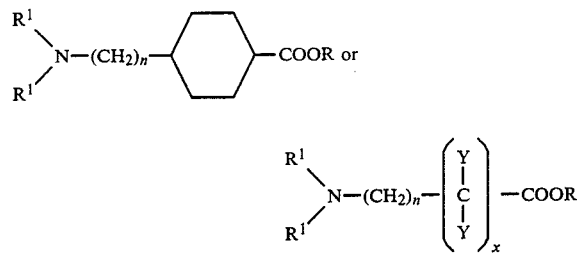

wherein $R^1$ is H or lower alkyl; n is an integer of from 1 to 6; x is 0 or 1; each Y is H; and R is H, lower alkyl or acyl; and the non-toxic, pharmaceutically acceptable salts thereof.

The lower alkyl moieties which may be employed in the practice of this invention are those which are straight or branch chained and possess six carbon atoms or less. The acyl moieties employed herein are those which are derived from hydrocarbon carboxylic acids of 12 carbon atoms or less, including among others, alkanoic acids, monocyclic aryl carboxylic acids and the like, as is known to and understood by the worker skilled in the art.

Most preferably, we have found that most satisfactory results are obtained when the liquid, parenterally administerable physiologically active compositions which are the subject of this invention have incorporated therein a small but effective amount of epsilonaminocaproic acid or transexamic acid, although the other compounds also provide acceptable results.

The compounds of Formulae (1) have been found to provide satisfactory results when incorporated into the subject liquid parenterally administerable, physiologically active compositions in small but effective amounts. We have found that the amounts of these compounds which may be employed herein should be sufficient to provide a final concentration thereof in the liquid, parenterally administerable, physiologically active composition to be administered to the patient, of from about 0.001M to about 0.75M. Preferably, in the practice of this invention the compounds of Formulae (I) may be present in the final, liquid, parenterally administerable, physiologically active compositions of this invention in a concentration of from about 0.05M to about 0.5M, and most preferably in a concentration of from about 0.1M to about 0.25M, although the other concentrations also provide satisfactory results.

The parenterally administerable, physiologically active compositions which may be employed in the practice of this invention include those parenterally administerable compositions which are stored and administered to the patient being treated in liquid form. More particularly, the compositions which may be employed in the practice of this invention are those which when administered, are in liquid form, for example, solutions, suspensions or mixtures, where the liquid vehicle is one which is a pharmaceutically acceptable liquid vehicle for parenteral administration, for example, water, oil, alcohol or the like, and which contains a physiologically active agent which is to be parenterally administered to the patient being treated. Parenteral administration of the final compositions of this invention may be accomplished by the administration thereof by any of the following routes: subcataneous, intradermal, intramuscular, or any other parenteral route usually employed for this purpose by the skilled worker employing whatever means are commonly used for such purposes, for example, hypodermic needle and syringe, and the like.

The physiologically active substances which may be employed in the practice of this invention are those substances which are to be parenterally administered to the patient and include substances which are parenterally administered for either therapeutic or diagnostic purposes. The physiologically active substances which may be employed include those pharmacologically active materials which may be of chemical or biological origin and include such substances as antibiotics, hormones, steroids, allergenic substances, allergen extracts, sera, vaccines, toxoids and anti-toxins. Preferably in the practice of the instant invention it is desired to employ those physiologically active substances which are derived from biological sources for example, antibiotics, allergenic materials and extracts, vaccines, and sera, for it has been determined that such biologically originated materials are most susceptible to storage instability and degradation. The amounts of the physiologically active substances which may be employed in the practice of this invention are those which are normally administered to the patients for the condition being treated or the purpose required, and will depend on the factors usually determined by the skilled worker to control the amounts of the substance being employed.

The final compositions of this invention may be prepared in any manner considered suitable by the skilled worker practicing the invention. The individual components of the final compositions of this invention may be admixed to form the desired compositions, or in some instances were the physiologically active substance is in a dry state, for example, as a result of lyophilization, the said physiologically active substance may first be reconstituted by the addition of the desired liquid vehicle, for example, pyrogen-free, distilled water and the required amounts of the compounds of Formulae (I) then incorporated, for example, by admixing, to yield the final storageably stable final compositions of this invention. In addition, should it be felt necessary, preservative agents, such as those known to the skilled worker may also be incorporated in the final compositions. The thus storageably stable final compositions may then be held for future use. The compounds of Formula (I) may be incorporated into the final parenterally administerable compositions of this invention at any time prior to the parenteral administration thereof to the patient being treated while still obtaining satisfactory results.

The invention may be further illustrated by the following examples:

EXAMPLE 1

Grass pollen extract (*Lolium perenne*) (commercially available from HAL Allergenen Laboratorium B.V., Haarlem, Holland) was admixed with 10 ml. of pyrogen-free, distilled water. To the resultant solution was added with mixing, epsilon-amino caproic acid until the resultant concentration thereof in the final solution was 0.1M. The resultant final composition was then divided into individual parenterally administerable doses of 0.05 ml. each.

EXAMPLE 2

The procedure of Example 1 was followed except that an equivalent amount of house dust mite extract (commercially available from HAL Allergenen Laboratorium B.V.) was substituted for the grass pollen extract, yielding equivalent results.

EXAMPLE 3

The procedure of Example 1 may be followed except that an equivalent amount of tranexamic acid may be substituted for epsilon-aminocaproic acid, with like results.

EXAMPLE 4

The procedure of Example 1 may be followed except that equivalent amounts of antibiotics, for example, penicillin G, cephalosporin, tetracycline or oxytetracycline; vaccines, for example, pertussis, typhoid, antirabies, or yellow fever vaccine; anti-toxin, for example, tetanus anti-toxin, may be substituted for the grass pollen extract, with similar results.

EXAMPLE 5

In vivo tests were performed employing the parenteral compositions of this invention. Grass pollen allergen extract and house dust mite allergen extracts were prepared in accordance with the procedures set forth in Example 1. In addition, as controls, compositions were prepared in accordance with the procedures of Example 1 and 2, except that sodium phosphate was substituted for epsilon-aminocaproic acid to a concentration of 0.15M.

The final parenterally administerable extracts had the following compositions:
  A. Grass pollen allergen in pyrogen-free distilled water containing 0.1M epsilon-aminocaproic acid.
  B. Grass pollen allergens in pyrogen-free distilled water containing 0.15M sodium phosphate.
  C. House dust mite allergens in pyrogen-free distilled water containing 0.1M epsilon-aminocaproic acid.
  D. House dust mite allergens in pyrogen-free distilled water containing 0.15M sodium phosphate.

The respective final extracts (0.05 ml) were intradermally injected into the test subjects forearms at various sites at premeasured distances from each other. These skin tests were read fifteen minutes after administration. The wheal and flare reactions were delineated on a transparent sheet and the mean square wheal diameters ($d^2wh$) were calculated. The results are set forth in FIG. 1 and show that there is a significant decrease in the local adverse reactions involved in the administration of the compositions of this invention.

EXAMPLE 6

Figure 2:
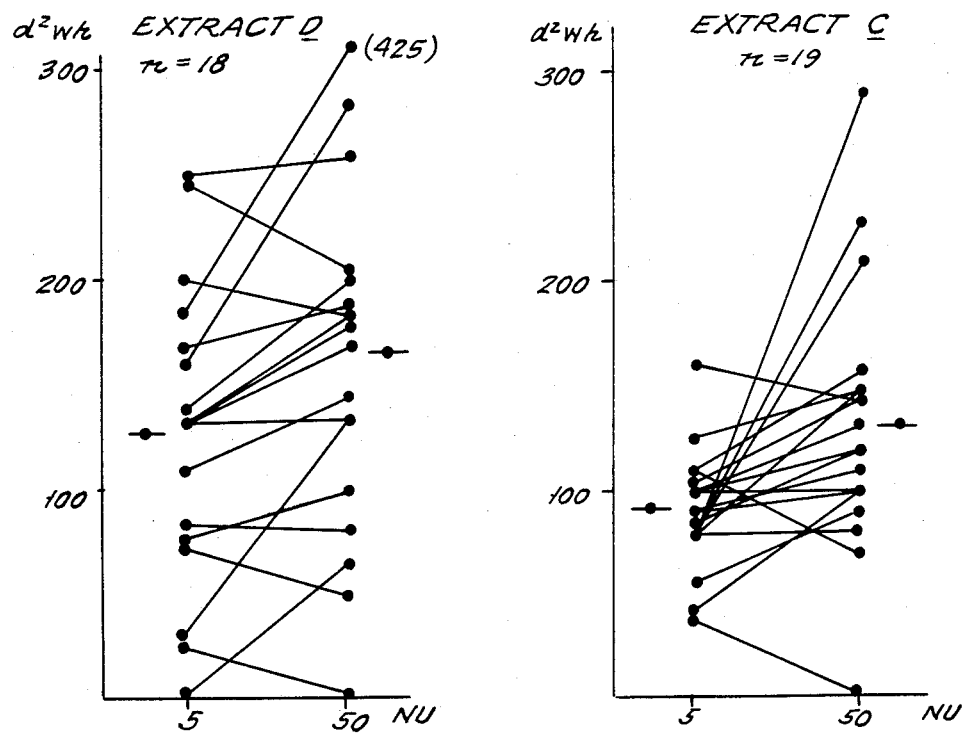

To several patients, two different dosages of Extracts C and D of Example 5 were administered. The initial dosage had a potency of 5 Noon Units (NU) while the second was increased tenfold to 50 NU. The difference in the skin reactivity as a result of the two administrations was measured in accordance with the method set forth in Example 5. The results set forth in FIG. 2 clearly show that the use of the compositions of the instant invention maintain a dose dependent reaction in a group of patients.

The invention may be variously otherwise embodied within the scope of the appended claims.

What is claimed is:

1. In a method of parenterally administering a physiologically active composition to a patient comprising inoculating a patient with a parenterally administerable composition comprised of a physiologically active substance selected from the group consisting of antibiotics, hormones, steroids, allergenic substances, allergen extracts, toxoids and anti-toxins, wherein the improvement comprises prior to the parenteral administration thereof, adding to the physiologically active composition an effective amount of a compound from the group consisting of:

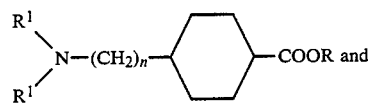 and

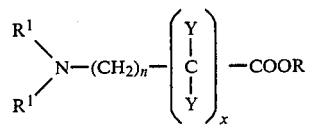

wherein $R^1$ is H or lower alkyl; n is an integer of from 1 to 6; x is 0 or 1; each Y is H; R is H, acyl or lower alkyl; and the non-toxic pharmaceutically acceptable salts thereof wherein the effective amount reduces local adverse reactions which occur at the site of administration.

2. The method of claim 1 wherein the compound is epsilon-aminocaproic acid.

3. The method of claim 1 wherein the compound is tranexamic acid.

4. The method of claim 1 wherein the physiologically active composition is selected, from the group consisting of an antibiotic, allergenic extract, toxoid and antitoxin.

5. The method of claim 1 wherein the physiologically active composition is an allergenic extract.

* * * * *